US012630506B2

(12) United States Patent
Matzuk et al.

(10) Patent No.: US 12,630,506 B2
(45) Date of Patent: May 19, 2026

(54) DIRECT THROMBIN INHIBITORS AND METHODS OF USE THEREOF

(71) Applicant: Baylor College of Medicine, Houston, TX (US)

(72) Inventors: Martin Matzuk, Houston, TX (US); Surendra Dawadi, Houston, TX (US); Melek Ucisik, Houston, TX (US); John Faver, Houston, TX (US); Kurt Bohren, Houston, TX (US); Feng Li, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 733 days.

(21) Appl. No.: 17/996,097

(22) PCT Filed: Apr. 16, 2021

(86) PCT No.: PCT/US2021/027584
§ 371 (c)(1),
(2) Date: Oct. 13, 2022

(87) PCT Pub. No.: WO2021/211913
PCT Pub. Date: Oct. 21, 2021

(65) Prior Publication Data
US 2023/0192606 A1 Jun. 22, 2023

Related U.S. Application Data

(60) Provisional application No. 63/011,439, filed on Apr. 17, 2020.

(51) Int. Cl.
*C07D 207/08* (2006.01)
*C07C 279/14* (2006.01)
*C07D 311/68* (2006.01)
*C07D 405/12* (2006.01)

(52) U.S. Cl.
CPC .......... *C07D 207/08* (2013.01); *C07C 279/14* (2013.01); *C07D 311/68* (2013.01); *C07D 405/12* (2013.01)

(58) Field of Classification Search
CPC .................................................... C07D 207/08
See application file for complete search history.

(56) References Cited

FOREIGN PATENT DOCUMENTS

WO 0222575 A1 3/2002

OTHER PUBLICATIONS

Acharya, et al., "Ace Revisited: A New Target for Structure-based Drug Design", Nature Reviews, Drug Discovery, vol. 2, No. 11, Nov. 1, 2003, pp. 891-902.
Agbowuro, et al., "Proteases and protease inhibitors in infectious diseases", Medicinal Research Reviews, vol. 38, No. 4, Jul. 2018, pp. 1295-1331, Wiley Periodicals, Inc.
Antermite, et al., "Regio- and Stereoselective Palladium-Catalyzed C($sp^3$)-H Arylation of Pyrrolidines and Piperidines with C(3) Directing Groups", Organic Letters, vol. 20, No. 13, Jun. 13, 2018, pp. 3948-3952.
Bachovchin, et al., "The Pharmacological Landscape and Therapeutic Potential of Serine Hydrolases", Nature Reviews, Drug Discovery, vol. 11, Jan. 3, 2012, pp. 52-68.
Barluenga, et al., "Novel PTP1B inhibitors identified by DNA display of fragment pairs", Bioorganic & Medicinal Chemistry Letters, vol. 26, No. 3, Feb. 1, 2016, pp. 1080-1085, Elsevier.
Berge, et al., "Pharmaceutical Salts", Journal of Pharmaceutical Sciences, vol. 66, No. 1, Jan. 1977, pp. 1-19, Elsevier.
Bernatowicz, et al., "1H-pyrazole-1-carboxamidine hydrochloride an Attractive Reagent for Guanylation of Amines and its Application to Peptide Synthesis", Journal of Organic Chemistry, vol. 57, No. 8, 1992, pp. 2497-2502.
Dawadi, et al., "Discovery of Potent Thrombin Inhibitors from a Protease-Focused DNA-Encoded Chemical Library", Proceedings of the National Academy of Sciences, vol. 117, No. 29, Jul. 21, 2020, pp. 16782-16789.
Deeks, et al., "HIV-1 Protease Inhibitors. A Review for Clinicians", JAMA, vol. 277, No. 2, Jan. 8, 1997, pp. 145-153.
Deng, et al., "Discovery of Highly Potent and Selective Small Molecule ADAMTS-5 Inhibitors That Inhibit Human Cartilage Degradation via Encoded Library Technology (ELT)", Journal of Medicinal Chemistry, vol. 55, No. 16, Aug. 23, 2012, pp. 7061-7079.
Du, et al., "A Mild, DNA-Compatible Nitro Reduction Using $B_2(OH)_4$", Organic Letters, vol. 21, 2019, pp. 2194-2199.
Du, et al., "DNA-Compatible Nitro Reduction and Synthesis of Benzimidazoles", Bioconjugate Chemistry, vol. 28, No. 10, Oct. 18, 2017, pp. 2575-2580.
Eatemadi, et al., "Role of protease and protease inhibitors in cancer pathogenesis and treatment", Biomedicine & Pharmacotherapy, vol. 86, Feb. 2017, pp. 221-231, Elsevier.
Faver, et al., "Quantitative Comparison of Enrichment from DNA-Encoded Chemical Library Selections", ACS Combinatorial Science, vol. 21, No. 2, Feb. 11, 2019, pp. 75-82.
Fear, et al., "Protease Inhibitors and Their Peptidomimetic Derivatives as Potential Drugs", Pharmacology & Therapeutics, vol. 113, No. 2, Feb. 2007, pp. 354-368.
Franco, et al., "Structure-based discovery of small molecule hepsin and HGFA protease inhibitors: Evaluation of potency and selectivity derived from distinct binding pockets", Bioorganic & Medicinal Chemistry, vol. 23, Issue 10, May 15, 2015, pp. 2328-2343, Elsevier.
Franzini, et al., "DNA-Encoded Chemical Libraries: Advancing beyond Conventional Small-Molecule Libraries", Accounts of Chemical Research, vol. 47, Mar. 28, 2014, pp. 1247-1255.
Goodnow, Jr., et al., "DNA-encoded Chemistry: Enabling the Deeper Sampling of Chemical Space", Nature Reviews, Drug Discovery, vol. 16, No. 2, Feb. 2017, pp. 131-147.

(Continued)

*Primary Examiner* — Golam M Shameem
(74) *Attorney, Agent, or Firm* — Kilpatrick Townsend & Stockton LLP

(57) ABSTRACT

Novel direct thrombin inhibitors are provided herein, along with methods for their use as anticoagulants. The direct thrombin inhibitors described herein are useful in treating and/or preventing thromboembolism and bleeding or clotting disorders. Also provided herein are methods for inhibiting thrombin in a cell using the compounds and compositions described herein.

20 Claims, 1 Drawing Sheet

(56) References Cited

OTHER PUBLICATIONS

Kikumoto, et al., "Selective Inhibition of Thrombin by (2R,4R)-4-methyl-1-[$N^2$-[(3-methyl-1,2,3,4-tetrahydro-8-quinolinyl)sulfonyl]-l-arginyl)]-2-piperidinecarboxylic acid", Biochemistry, vol. 23, No. 1, Jan. 3, 1984, pp. 85-90, American Chemical Society.
Klein, et al., "Proteolytic Cleavage-Mechanisms, Function, and "Omic" Approaches for a Near-Ubiquitous Posttranslational Modification", Chemical Reviews, vol. 118, No. 3, Feb. 14, 2018, pp. 1137-1168.
Lerner, et al., "DNA-Encoded Compound Libraries as Open Source: A Powerful Pathway to New Drugs", Angewandte Chemie International, vol. 56, 2017, pp. 1164-1165.
Lu, et al., "Oxyguanidines. Part 2: Discovery of a Novel Orally Active Thrombin Inhibitor Through Structure-Based Drug Design and Parallel Synthesis", Bioorganic & Medicinal Chemistry Letters, vol. 14, No. 14, May 28, 2004, pp. 3727-3731.
Ma, et al., "Functionality-Independent DNA Encoding of Complex Natural Products", Angewandte Chemie, vol. 58, No. 27, May 22, 2019, pp. 9254-9261, Wiley-VCH Verlag GmbH & Co. KGaA, Weinheim, Germany.
Mannocci, et al., "Isolation of Potent and Specific Trypsin Inhibitors From a DNA-encoded Chemical Library", Bioconjugate Chemistry, vol. 21, No. 10, Oct. 20, 2010, pp. 1836-1841, American Chemical Society.
Neri, et al., "DNA-Encoded Chemical Libraries: A Selection System Based on Endowing Organic Compounds with Amplifiable Information", Annual Review of Biochemistry, vol. 87, Jan. 12, 2018, pp. 479-502.
Neri, "Twenty-five Years of DNA-Encoded Chemical Libraries", ChemBioChem, Available online at: file:///C:/Users/U6060461/Music/NPL_NERI_2017.pdf, 2017, pp. 827-828.
Nutescu, et al., "Direct Thrombin Inhibitors for Anticoagulation", Cardiology, The Annals of Pharmacotherapy, vol. 38, Jan. 2004, pp. 99-109.
Okamoto, et al., "Potent Inhibition of Thrombin by the Newly Synthesized Arginine Derivative No. 805. The Importance of Stereo-structure of its Hydrophobic Carboxamide Portion", Biochemical and Biophysical Research Communications, vol. 101, Issue 2, Jul. 30, 1981, pp. 440-446.
PCT/US2021/027584, "International Search Report and Written Opinion", Jun. 7, 2021, 12 pages.
PCT/US2021/027584, "International Preliminary Report on Patentability", Oct. 27, 2022, 8 pages.
Satz, et al., "DNA Compatible Multistep Synthesis and Applications to DNA Encoded Libraries", Bioconjugate Chemistry, vol. 26, No. 8, Aug. 19, 2015, pp. 1623-1632.
Stress, et al., "A DNA-Encoded Chemical Library Incorporating Elements of Natural Macrocycles", Angewandte Chemie (International ed. in English), vol. 58, No. 28, Jul. 8, 2019, pp. 9570-9574, ChemRxiv.
Wagner, et al., "Rational Design, Synthesis, and X-ray Structure of Selective Noncovalent Thrombin Inhibitors", Journal of Medicinal Chemistry, vol. 41, No. 19, Sep. 10, 1998, pp. 3664-3674, American Chemical Society.
Yuen, et al., "A Focused DNA-Encoded Chemical Library for the Discovery of Inhibitors of $NAD^+$-Dependent Enzymes", Journal of the American Chemical Society, vol. 141, No. 13, Mar. 11, 2019, pp. 5169-5181.
Zambaldo, et al., "Screening for Covalent Inhibitors Using DNA-display of Small Molecule Libraries Functionalized with Cysteine Reactive Moieties", Medicinal Chemistry Communication, vol. 7, Jan. 2016, pp. 1340-1351.

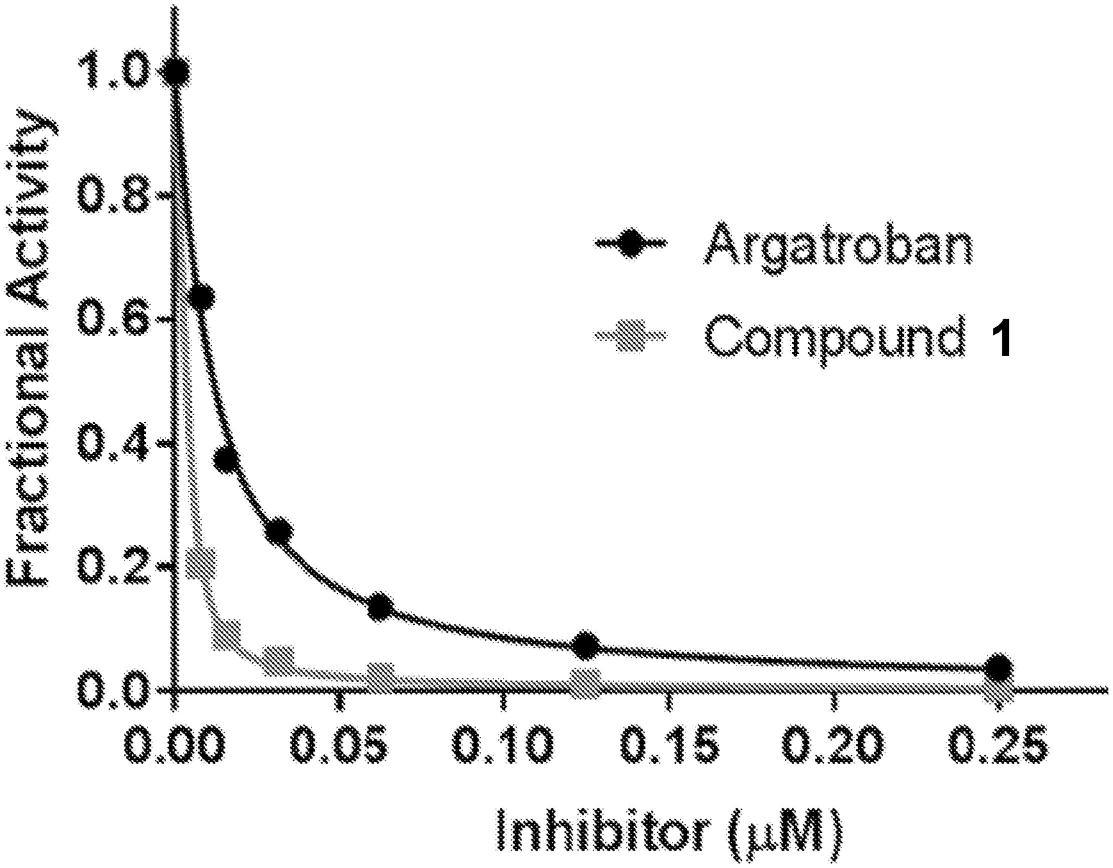
Fractional Activity
1.0
0.8
0.6
0.4
0.2
0.0
0.00
0.05
0.10
0.15
0.20
0.25
Inhibitor (μM)
Argatroban
Compound 1

DIRECT THROMBIN INHIBITORS AND METHODS OF USE THEREOF

CROSS-REFERENCE TO PRIORITY APPLICATION

This application claims priority to U.S. Provisional Application No. 63/011,439, filed Apr. 17, 2020, which is incorporated herein by reference in its entirety.

STATEMENT REGARDING FEDERALLY FUNDED RESEARCH

This invention was made with government support under Grant No. P01HD087157, awarded by the National Institutes of Health. The government has certain rights in the invention.

BACKGROUND

Proteases are enzymes that catalyze the hydrolysis of peptidic bonds in proteins. Proteases have been an intensely studied class of drug discovery targets due to their involvement in various pathophysiological processes, with key roles in protein degradation and signaling pathways. Mechanistically, proteases generally fall into five classes, including cysteine proteases, serine proteases, metalloproteases, threonine proteases, and aspartic proteases. After activation of the amide with key residues, the cysteine, serine, and threonine protease classes utilize the namesake residue to attack the amide carbonyl group. Metalloproteases and aspartic proteases use an activated water. Clinically, there have been numerous successes by targeting proteases, including the development of inhibitors of angiotensin-converting enzyme (ACE) for cardiovascular disorders, thrombin inhibitors for thromboembolism and bleeding disorders, and HIV protease inhibitors in the treatment of HIV and AIDS, among others.

SUMMARY

Described herein are novel direct thrombin inhibitors and methods for their use as anticoagulants. The direct thrombin inhibitors described herein are useful in treating and/or preventing thromboembolism and bleeding disorders and/or clotting disorders. The methods include administering to a subject a compound as described herein.

A class of direct thrombin inhibitors as described herein includes compounds of the following formula:

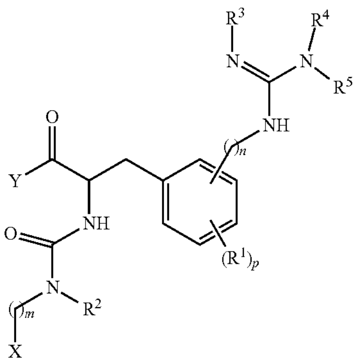

or a pharmaceutically acceptable salt or prodrug thereof, wherein m and n are each independently 0, 1, or 2; p is 1, 2, 3, or 4; X is substituted or unsubstituted aryl, substituted or unsubstituted heteroaryl, substituted or unsubstituted cycloalkyl, or substituted or unsubstituted heterocycloalkyl; Y is hydroxy, alkoxy, aryloxy, substituted or unsubstituted amino, substituted or unsubstituted cycloalkyl, or substituted or unsubstituted heterocycloalkyl; each $R^1$ is independently selected from the group consisting of hydrogen, halogen, cyano, trifluoromethyl, alkoxy, aryloxy, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^2$, $R^3$, $R^4$, and $R^5$ are each independently selected from the group consisting of hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl. Optionally, $R^3$, $R^4$, and $R^5$ are each hydrogen. In some cases, $R^2$ is methyl. Optionally, X is substituted or unsubstituted phenyl or X is substituted or unsubstituted chromanyl. In some cases, n is 1.

Optionally, the compound has the following formula:

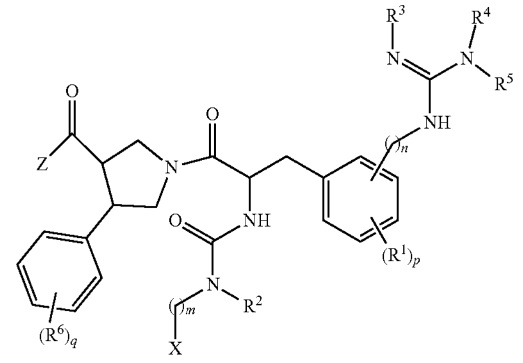

or a pharmaceutically acceptable salt or prodrug thereof, wherein q is 1, 2, 3, 4, or 5; each $R^6$ is independently selected from the group consisting of hydrogen, halogen, cyano, trifluoromethyl, alkoxy, aryloxy, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and Z is $-NR^7R^8$ or $-OR^7$, wherein $R^7$ and $R^8$ are each independently selected from the group consisting of hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl. Optionally, $R^2$ is methyl. Optionally, $R^6$ is alkoxy (e.g., p-methoxy).

Optionally, the compound has the following formula:

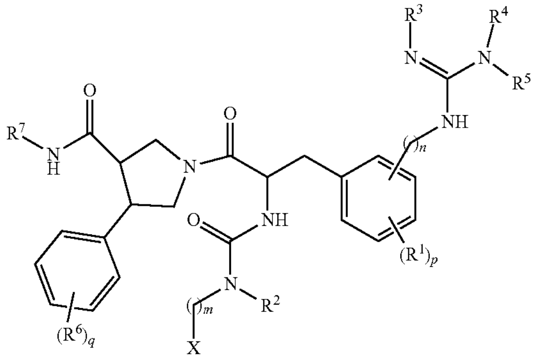

or a pharmaceutically acceptable salt or prodrug thereof.

Optionally, the compound has the following formula;

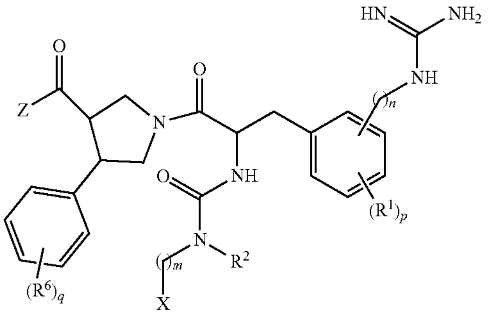

or a pharmaceutically acceptable salt or prodrug thereof.

Optionally, the compound has the following formula:

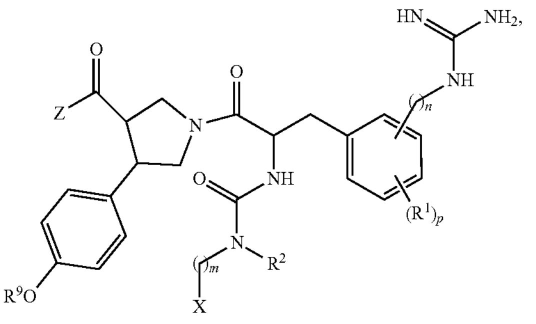

or a pharmaceutically acceptable salt or prodrug thereof, wherein $R^9$ is substituted or unsubstituted alkyl or substituted or unsubstituted aryl.

Optionally, the compound has the following formula:

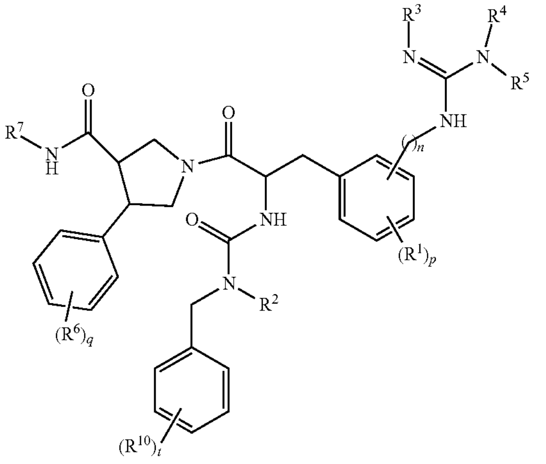

or a pharmaceutically acceptable salt or prodrug thereof, wherein t is 0, 1, 2, 3, 4, or 5; and each $R^{10}$ is independently hydrogen, halogen, cyano, trifluoromethyl, alkoxy, aryloxy, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl.

Optionally, the compound has the following formula:

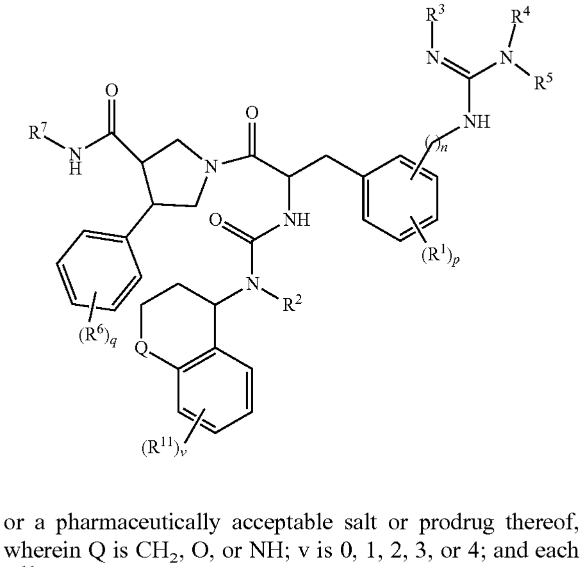

or a pharmaceutically acceptable salt or prodrug thereof, wherein Q is $CH_2$, O, or NH; v is 0, 1, 2, 3, or 4; and each $R^{11}$ is independently hydrogen, halogen, cyano, trifluoromethyl, alkoxy, aryloxy, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl.

Optionally, the compound has the following formula:

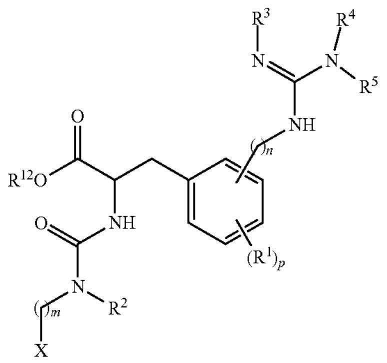

or a pharmaceutically acceptable salt or prodrug thereof, wherein $R^{12}$ is hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl.

Optionally, the compound has the following formula:

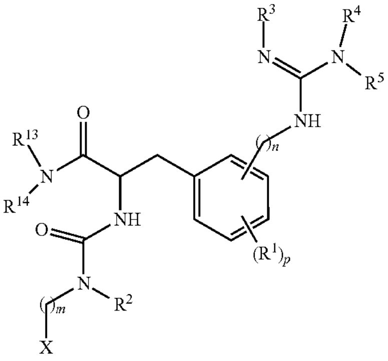

or a pharmaceutically acceptable salt or prodrug thereof, wherein $R^{13}$ and $R^{14}$ are each independently selected from the group consisting of hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Optionally, the compound is selected from the group consisting of:

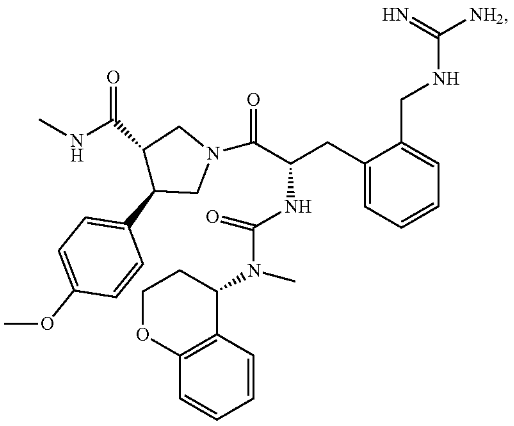

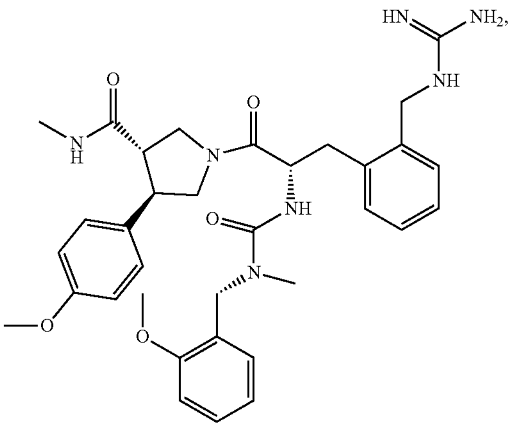

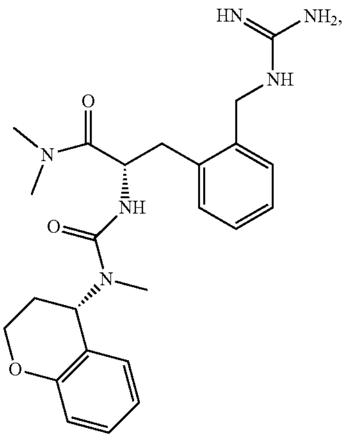

-continued

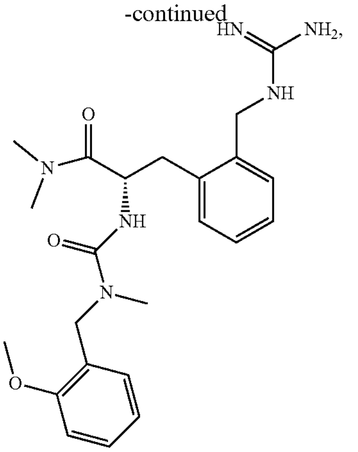

and

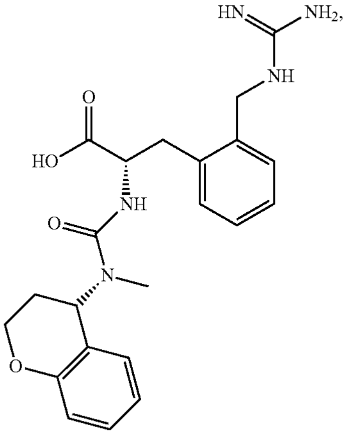

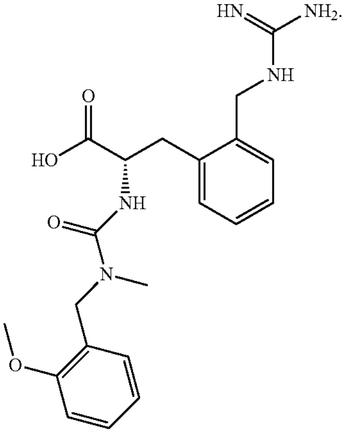

Also described herein is a pharmaceutical composition, comprising a compound as described herein and a pharmaceutically acceptable carrier.

Further described is a kit comprising a compound or a pharmaceutical composition as described herein.

Methods of using the compounds and pharmaceutical compositions as described herein are also provided. A method of treating or preventing thromboembolism in a subject is provided herein, the method comprising administering to the subject an effective amount of a compound or a pharmaceutical composition as described above. A method of treating or preventing a bleeding disorder in a subject is provided herein, the method comprising administering to the subject an effective amount of a compound or a pharmaceutical composition as described above. Optionally, the bleeding disorder is selected from the group consisting of acute coronary syndrome, atrial fibrillation, coronary artery disease, hypercoagulable states, unstable angina, myocardial infarction, ischemic stroke, deep vein thrombosis, peripheral occlusive arterial disease, transient ischemic attack, restenosis, cardiopulmonary bypass, heart failure, pulmonary embolism, disseminated intravascular coagulation, hemophilia, hereditary hemorrhagic telangiectasia, an open wound, thrombocytopenia, and von Willebrand disease.

Also described herein are methods of inhibiting thrombin in a cell. A method of inhibiting thrombin in a cell comprises contacting the cell with an effective amount of a compound or a pharmaceutical composition as described herein. The contacting can be performed in vitro or in vivo.

The details of one or more embodiments are set forth in the drawing and the description below. Other features, objects, and advantages will be apparent from the description and drawing, and from the claims.

DESCRIPTION OF THE DRAWING

FIG. 1 is a dose-response curve of thrombin inhibition by Compound 1 and known anticoagulant argatroban.

DETAILED DESCRIPTION

Described herein are novel direct thrombin inhibitors and methods for their use as anticoagulants. The direct thrombin inhibitors described herein are useful in treating and/or preventing thromboembolism and bleeding and/or clotting disorders.

I. Compounds

A class of compounds described herein includes compounds of Formula I:

Formula I

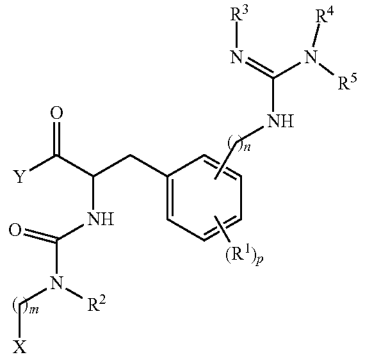

and pharmaceutically acceptable salts or prodrugs thereof.

In Formula I, m and n are each independently 0, 1, or 2.

Also, in Formula I, p is 1, 2, 3, or 4.

Additionally, in Formula I, X is substituted or unsubstituted aryl, substituted or unsubstituted heteroaryl, substituted or unsubstituted cycloalkyl, or substituted or unsubstituted heterocycloalkyl. Optionally, X is substituted or unsubstituted phenyl or substituted or unsubstituted chromanyl.

Further, in Formula I, Y is hydroxy, alkoxy, aryloxy, substituted or unsubstituted amino, substituted or unsubstituted cycloalkyl, or substituted or unsubstituted heterocycloalkyl.

Also, in Formula I, each $R^1$ is independently selected from hydrogen, halogen, cyano, trifluoromethyl, alkoxy, aryloxy, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Additionally, in Formula I, $R^2$, $R^3$, $R^4$, and $R^5$ are each independently selected from hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl. Optionally, $R^2$ is substituted or unsubstituted alkyl (e.g., methyl). Optionally, $R^3$, $R^4$, and $R^5$ are each hydrogen.

In some cases, the compounds according to Formula I are represented by Structure I-A:

Structure I-A

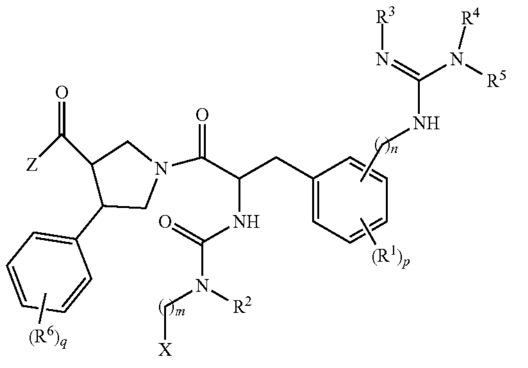

or a pharmaceutically acceptable salt or prodrug thereof.

In Structure I-A, m, n, p, X, $R^1$, $R^2$, $R^3$, $R^4$, and $R^5$ are as defined for Formula I.

Also, in Structure I-A, q is 1, 2, 3, 4, or 5.

Additionally, in Structure I-A, each $R^6$ is independently selected from hydrogen, halogen, cyano, trifluoromethyl, alkoxy, aryloxy, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl. Optionally, one or more of the $R^6$ groups is alkoxy. Optionally. $R^6$ is p-methoxy.

Further, in Structure I-A, Z is —$NR^7R^8$ or —$OR^7$, wherein $R^7$ and $R^8$ are each independently selected from hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

In some cases, the compounds according to Structure I-A are represented by Substructure I-A1:

Structure I-A1

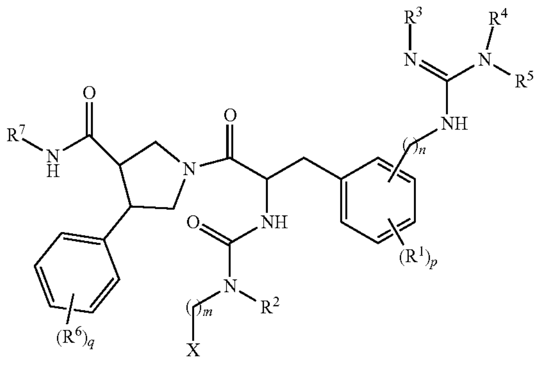

or a pharmaceutically acceptable salt or prodrug thereof.

In Substructure I-A1, m, n, p, q, X, $R^1$, $R^2$, $R^3$, $R^4$, $R^5$, $R^6$, and $R^7$ are as defined above for Structure I-A.

In some cases, the compounds according to Structure I-A are represented by Substructure I-A2:

Substructure I-A2

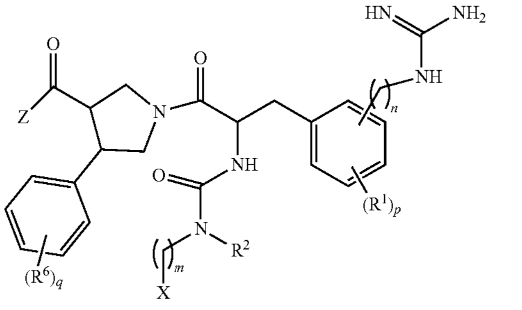

or a pharmaceutically acceptable salt or prodrug thereof.

In Substructure I-A2, m, n, p, q, X, Z, $R^1$, $R^2$, and $R^6$ are as defined above for Structure I-A.

In some cases, the compounds according to Structure I-A are represented by Substructure I-A3:

Substructure I-A3

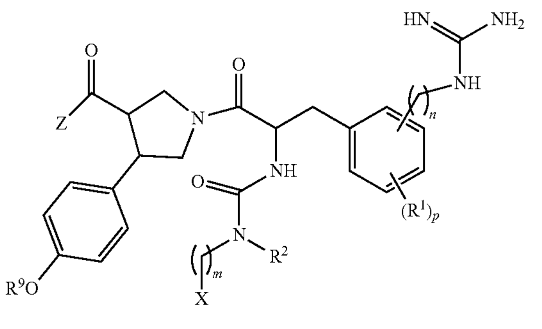

or a pharmaceutically acceptable salt or prodrug thereof.

In Substructure I-A3, m, n, p, X, Z, $R^1$, and $R^2$ are as defined above for Structure I-A.

Also in Substructure I-A3, $R^9$ is substituted or unsubstituted alkyl or substituted or unsubstituted aryl.

In some cases, the compounds according to Structure I-A are represented by Substructure I-A4:

Substructure I-A4

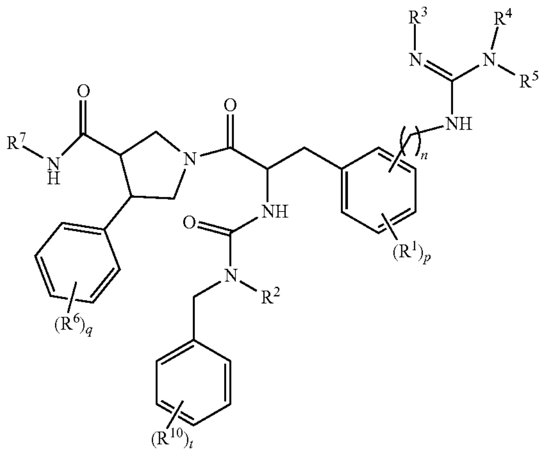

or a pharmaceutically acceptable salt or prodrug thereof.

In Substructure I-A4, n, p, q, $R^1$, $R^2$, $R^3$, $R^4$, $R^5$, $R^6$, and $R^7$ are as defined above for Structure I-A.

Also, in Substructure I-A4, t is 0, 1, 2, 3, 4, or 5.

Additionally, in Substructure I-A4, each $R^{10}$ is independently hydrogen, halogen, cyano, trifluoromethyl, alkoxy, aryloxy, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl.

In some cases, the compounds according to Structure I-A are represented by Substructure I-A5:

Substructure I-A5

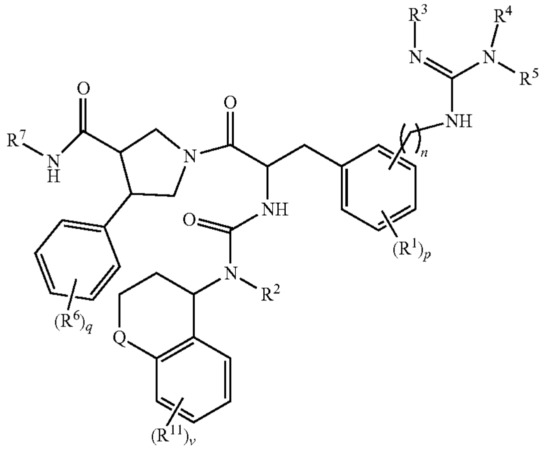

or a pharmaceutically acceptable salt or prodrug thereof.

In Substructure I-A5, n, p, q, $R^1$, $R^2$, $R^3$, $R^4$, $R^5$, $R^6$, and $R^7$ are as defined above for Structure I-A.

Also, in Substructure I-A5, Q is $CH_2$, O, or NH.

Additionally, in Substructure I-A5, v is 0, 1, 2, 3, or 4.

Further, in Substructure I-A5, each $R^{11}$ is independently hydrogen, halogen, cyano, trifluoromethyl, alkoxy, aryloxy, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl.

In some cases, the compounds according to Formula I are represented by Structure I-B:

Structure I-B

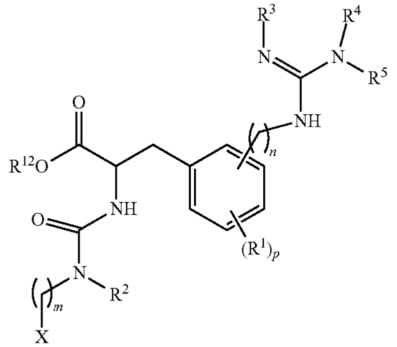

or a pharmaceutically acceptable salt or prodrug thereof.

In Structure I-B, m, n, p, X, $R^1$, $R^2$, $R^3$, $R^4$, and $R^5$ are as defined for Formula I.

Also in Structure I-B, $R^{12}$ is hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl.

In some cases, the compounds according to Formula I are represented by Structure I-C:

Structure I-C

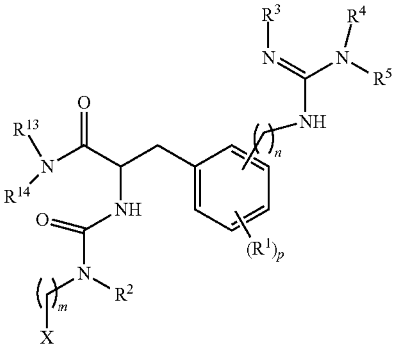

or a pharmaceutically acceptable salt or prodrug thereof.

In Structure I-C, m, n, p, X, $R^1$, $R^2$, $R^3$, $R^4$, and $R^5$ are as defined above for Formula I.

Also in Structure I-C, $R^{13}$ and $R^{14}$ are each independently selected from hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Examples of Formula I include the following compounds:

Compound 1

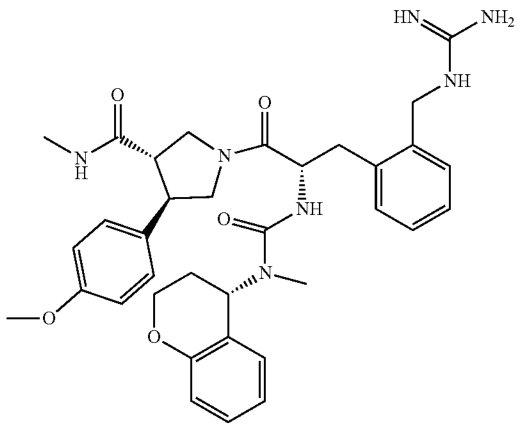

Compound 2

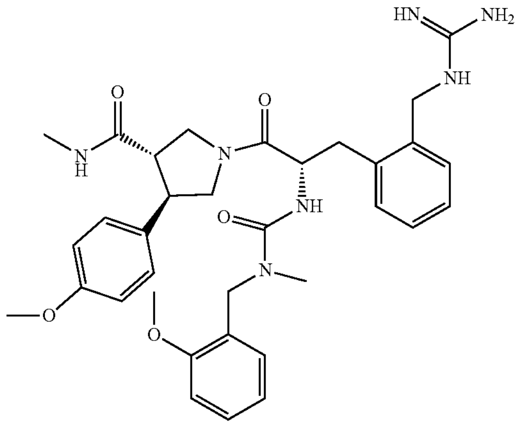

Compound 3

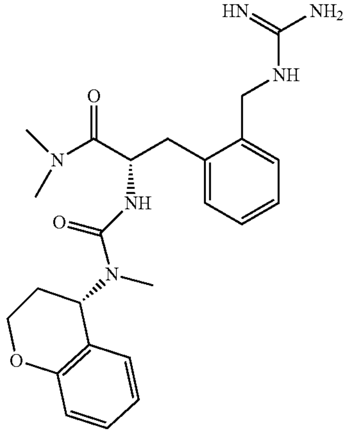

-continued

Compound 4

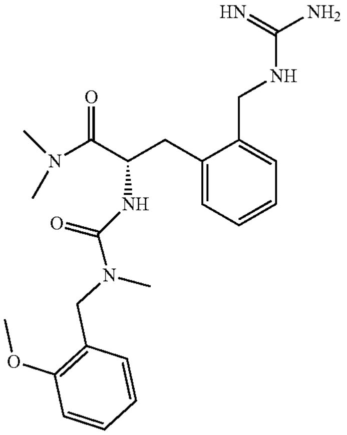

Compound 5

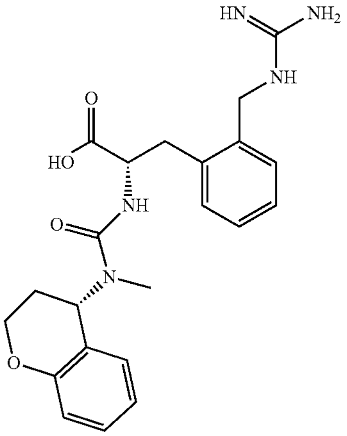

Compound 6

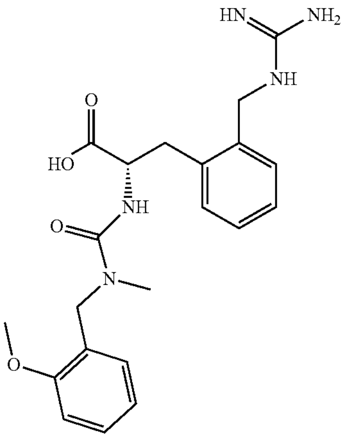

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

Heteroalkyl, heteroalkenyl, and heteroalkynyl are defined similarly as alkyl, alkenyl, and alkynyl, but can contain O, S, or N heteroatoms or combinations thereof within the backbone. Ranges of these groups useful with the compounds and methods described herein include $C_1$-$C_{20}$ heteroalkyl, $C_2$-$C_{20}$ heteroalkenyl, and $C_2$-$C_{20}$ heteroalkynyl. Additional ranges of these groups useful with the compounds and methods described herein include $C_1$-$C_{12}$ heteroalkyl, $C_2$-$C_{12}$ heteroalkenyl, $C_2$-$C_{12}$ heteroalkynyl, $C_1$-$C_6$ heteroalkyl, $C_2$-$C_6$ heteroalkenyl, $C_2$-$C_6$ heteroalkynyl, $C_1$-$C_4$ heteroalkyl, $C_2$-$C_4$ heteroalkenyl, and $C_2$-$C_4$ heteroalkynyl.

The terms cycloalkyl, cycloalkenyl, and cycloalkynyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_{20}$ cycloalkyl, $C_4$-$C_{20}$ cycloalkenyl, and $C_4$-$C_{20}$ cycloalkynyl. Additional ranges of these groups useful with the compounds and methods described herein include $C_5$-$C_{12}$ cycloalkyl, $C_5$-$C_{12}$ cycloalkenyl, $C_5$-$C_{12}$ cycloalkynyl, $C_5$-$C_6$ cycloalkyl, $C_5$-$C_6$ cycloalkenyl, and $C_5$-$C_6$ cycloalkynyl.

The terms heterocycloalkyl, heterocycloalkenyl, and heterocycloalkynyl are defined similarly as cycloalkyl, cycloalkenyl, and cycloalkynyl, but can contain O, S, or N heteroatoms or combinations thereof within the cyclic backbone. Ranges of these groups useful with the compounds and methods described herein include $C_3$-$C_{20}$ heterocycloalkyl, $C_3$-$C_{20}$ heterocycloalkenyl, and $C_3$-$C_{20}$ heterocycloalkynyl. Additional ranges of these groups useful with the compounds and methods described herein include $C_3$-$C_{12}$ heterocycloalkyl, $C_5$-$C_{12}$ heterocycloalkenyl, $C_5$-$C_{12}$ heterocycloalkynyl, $C_5$-$C_6$ heterocycloalkyl, $C_5$-$C_6$ heterocycloalkenyl, and $C_5$-$C_6$ heterocycloalkynyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline. The aryl and heteroaryl molecules can be attached at any position on the ring, unless otherwise noted.

The term alkoxy as used herein is an alkyl group bound through a single, terminal ether linkage. The term aryloxy as used herein is an aryl group bound through a single, terminal ether linkage. Likewise, the terms alkenyloxy, alkynyloxy, heteroalkyloxy, heteroalkenyloxy, heteroalkynyloxy, heteroaryloxy, cycloalkyloxy, and heterocycloalkyloxy as used herein are an alkenyloxy, alkynyloxy, heteroalkyloxy, heteroalkenyloxy, heteroalkynyloxy, heteroaryloxy, cycloalkyloxy, and heterocycloalkyloxy group, respectively, bound through a single, terminal ether linkage.

The term hydroxy as used herein is represented by the formula —OH.

The terms amine or amino as used herein are represented by the formula $—NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The alkoxy, aryloxy, amino, alkyl, alkenyl, alkynyl, aryl, heteroalkyl, heteroalkenyl, heteroalkynyl, heteroaryl, cycloalkyl, or heterocycloalkyl molecules used herein can be substituted or unsubstituted. As used herein, the term substituted includes the addition of an alkoxy, aryloxy, amino, alkyl, alkenyl, alkynyl, aryl, heteroalkyl, heteroalkenyl, heteroalkynyl, heteroaryl, cycloalkyl, or heterocycloalkyl group to a position attached to the main chain of the alkoxy, aryloxy, amino, alkyl, alkenyl, alkynyl, aryl, heteroalkyl, heteroalkenyl, heteroalkynyl, heteroaryl, cycloalkyl, or heterocycloalkyl, e.g., the replacement of a hydrogen by one of these molecules. Examples of substitution groups include, but are not limited to, hydroxy, halogen (e.g., F, Br, Cl, or I), and carboxyl groups. Conversely, as used herein, the term unsubstituted indicates the alkoxy, aryloxy, amino, alkyl, alkenyl, alkynyl, aryl, heteroalkyl, heteroalkenyl, heteroalkynyl, heteroaryl, cycloalkyl, or heterocycloalkyl has a full complement of hydrogens, i.e., commensurate with its saturation level, with no substitutions, e.g., linear decane ($—(CH_2)_9—CH_3$).

II. Methods of Making the Compounds

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formula I include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

An exemplary synthetic method, which can be modified by one of skill in the art to synthesize the compounds described herein, is provided in Example 1.

III. Pharmaceutical Formulations

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22d Edition, Loyd et al. eds., Pharmaceutical Press and Philadelphia College of Pharmacy at University of the Sciences (2012). Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, NJ), polyethylene glycol (PEG), and PLURONICS™ (BASF; Florham Park, NJ).

Compositions containing the compound described herein or derivatives thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol. (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, inhalants, and skin patches. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

Optionally, the compounds described herein can be contained in a drug depot. A drug depot comprises a physical structure to facilitate implantation and retention in a desired site (e.g., a synovial joint, a disc space, a spinal canal, abdominal area, a tissue of the patient, etc.). The drug depot can provide an optimal concentration gradient of the compound at a distance of up to about 0.1 cm to about 5 cm from the implant site. A depot, as used herein, includes but is not limited to capsules, microspheres, microparticles, microcapsules, microfibers particles, nanospheres, nanoparticles, coating, matrices, wafers, pills, pellets, emulsions, liposomes, micelles, gels, antibody-compound conjugates, protein-compound conjugates, or other pharmaceutical delivery compositions. Suitable materials for the depot include pharmaceutically acceptable biodegradable materials that are preferably FDA approved or GRAS materials. These materials can be polymeric or non-polymeric, as well as synthetic or naturally occurring, or a combination thereof. The depot can optionally include a drug pump.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., J. Pharm. Sci. (1977) 66, 1, which is incorporated herein by reference in its entirety, at least, for compositions taught therein.)

Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.0001 to about 200 mg/kg of body weight of active compound per day, which may be administered in a single dose or in the form of individual divided doses, such as from 1 to 4 times per day. Alternatively, the dosage amount can be from about 0.01 to about 150 mg/kg of body weight of active compound per day, about 0.1 to 100 mg/kg of body weight of active compound per day, about 0.5 to about 75 mg/kg of body weight of active compound per day, about 0.5 to about 50 mg/kg of body weight of active compound per day, about 0.01 to about 50 mg/kg of body weight of active compound per day, about 0.05 to about 25 mg/kg of body weight of active compound per day, about 0.1 to about 25 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, about 5 mg/kg of body weight of active compound per day, about 2.5 mg/kg of body weight of active compound per day, about 1.0 mg/kg of body weight of active compound per day, or about 0.5 mg/kg of body weight of active compound per day, or any range derivable therein. Optionally, the dosage amounts are from about 0.01 mg/kg to about 10 mg/kg of body weight of active compound per day. Optionally, the dosage amount is from about 0.01 mg/kg to about 5 mg/kg. Optionally, the dosage amount is from about 0.01 mg/kg to about 2.5 mg/kg.

Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems. Further, depending on the route of administration, one of skill in the art would know how to determine doses that result in a plasma concentration for a desired level of response in the cells, tissues and/or organs of a subject.

IV. Methods of Use

Provided herein are methods to treat or prevent thromboembolism or a bleeding disorder in a subject. The methods include administering to the subject an effective amount of one or more of the compounds or compositions described herein, or a pharmaceutically acceptable salt or prodrug thereof. Effective amount, when used to describe an amount of compound in a method, refers to the amount of a compound that achieves the desired pharmacological effect or other biological effect. The effective amount can be, for example, the concentrations of compounds at which thrombin is inhibited in vitro, as provided herein. Also contemplated is a method that includes administering to the subject an amount of one or more compounds described herein such that an in vivo concentration at a target cell in the subject corresponding to the concentration administered in vitro is achieved. Optionally, the methods described herein include selecting a subject in need of controlled clot formation and administering to the subject an effective amount of one or more of the compounds or compositions described herein. Clot formation can be controlled by inhibiting thrombin, for example.

The compounds and compositions described herein or pharmaceutically acceptable salts thereof are useful for treating thromboembolism or bleeding and/or clotting disorders in humans, including, without limitation, pediatric and geriatric populations, and in animals, e.g., veterinary applications.

In some examples, the bleeding disorder and/or clotting disorder is or is associated with acute coronary syndrome, atrial fibrillation, coronary artery disease, hypercoagulable states, unstable angina, myocardial infarction, ischemic stroke, deep vein thrombosis, peripheral occlusive arterial disease, transient ischemic attack, restenosis, cardiopulmonary bypass, heart failure, pulmonary embolism, disseminated intravascular coagulation, hemophilia, hereditary hemorrhagic telangiectasia, an open wound, thrombocytopenia, or von Willebrand disease. Optionally, the bleeding and/or clotting disorder is associated with or triggered by blood transfusion, dialysis, or other medical procedures or implants (e.g., heart valves or stents).

The methods of treating or preventing thromboembolism or bleeding and/or clotting disorders in a subject can further comprise administering to the subject one or more additional agents. The one or more additional agents and the compounds described herein or pharmaceutically acceptable salts or prodrugs thereof can be administered in any order, including concomitant, simultaneous, or sequential administration. Sequential administration can be administration in a temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Additional therapeutic agents include, but are not limited to, anticoagulants, including direct thrombin inhibitors, coumarin anticoagulants, heparins, and Factor Xa inhibitors. Exemplary direct thrombin inhibitors that can be used as additional therapeutic agents include, for example, dabigatran, argatroban, inogatran, melagatran, ximelagatran, hirudin, bivalirudin, lepirudin, and desirudin. Other exemplary anticoagulants include heparin, warfarin, rivaroxaban, dabigatran, apixaban, edoxaban, enoxaparin, fondaparinux, clopidogrel, ticagrelor, prasugrel, dipyridamole, aspirin, dipyridamole/aspirin, ticlopidine, and eptifibatide.

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of thromboembolism or a bleeding and/or clotting disorder), during early onset (e.g., upon initial signs and symptoms of thromboembolism or a bleeding and/or clotting disorder), or after the development of thromboembolism or a bleeding and/or clotting disorder. Prophylactic administration can occur for several days to years prior to the manifestation of symptoms of thromboembolism or a bleeding disorder. Therapeutic treatment involves administering to a subject a therapeutically effective amount of the compounds and compositions or pharmaceutically acceptable salts thereof as described herein after thromboembolism or a bleeding and/or clotting disorder is diagnosed.

The methods herein for prophylactic and therapeutic treatment optionally comprise selecting a subject with or at risk of developing thromboembolism or a bleeding and/or clotting disorder. A skilled artisan can make such a determination using, for example, a variety of prognostic and diagnostic methods, including, for example, a personal or family history of the disease or condition, clinical tests (e.g., imaging, genetic tests), and the like.

The compounds and compositions described herein are also useful in inhibiting thrombin in a cell. The methods for inhibiting thrombin in a cell include contacting a cell with an effective amount of one or more of the compounds or a composition as described herein. Optionally, the contacting is performed in vivo. Optionally, the contacting is performed in vitro.

V. Kits

Also provided herein are kits for treating or preventing thromboembolism or bleeding and/or clotting disorders in a subject. A kit can include any of the compounds or compositions described herein. For example, a kit can include one or more compounds of Formula I. A kit can further include one or more additional agents, such as one or more anticoagulants. A kit can include an oral formulation of any of the compounds or compositions described herein. A kit can include an intravenous formulation of any of the compounds or compositions described herein. A kit can additionally include directions for use of the kit (e.g., instructions for treating a subject), a container, a means for administering the compounds or compositions (e.g., a syringe), and/or a carrier.

As used herein the terms treatment, treat, or treating refer to a method of reducing one or more symptoms of a disease or condition. Thus in the disclosed method, treatment can refer to a 10%, 20%, 30%, 40%, 50%, 60%, 70%, 80%, 90%, or 100% reduction in the severity of one or more symptoms of the disease or condition. For example, a method for treating a disease is considered to be a treatment if there is a 10% reduction in one or more symptoms or signs of the disease in a subject as compared to a control. As used herein, control refers to the untreated condition. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compositions described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the subject matter described herein which are apparent to one skilled in the art.

Example 1: Synthesis of Compounds

Compound 1 was synthesized according to the methods depicted in Schemes 1 and 2. Specifically, intermediate 10 was prepared using the method shown in Scheme 1, and was then used to prepare Compound 1 as shown in Scheme 2.

Scheme 1

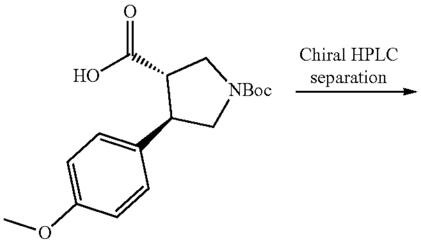

racemic trans 7

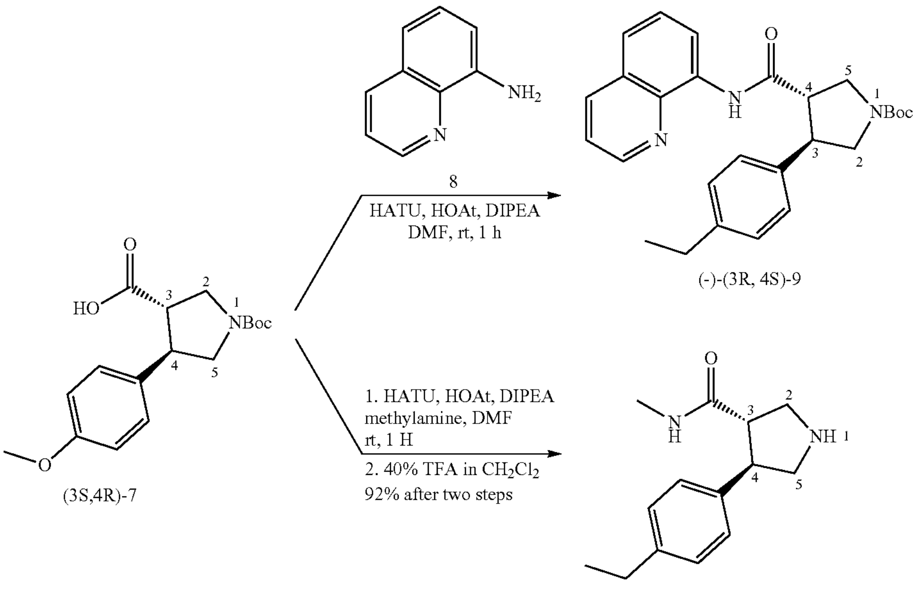

8

(-)-(3R, 4S)-9

(3S,4R)-7

(3S,4R)-10

The enantiomers of racemic trans 7 were separated by prep-HPLC equipped with a chiral column with retention times of 9 and 11 minutes. The absolute configuration of each enantiomer was determined by chemical derivatization to a given compound 9. The enantiomers of 7 were each coupled with 8-aminoquinoline 8 to give two enantiomers of 9. The enantiomer of 7, with a retention time of 9 minutes, provided the (−)-(3R,4S)-9, which confirms this is the 3S,4R isomer of 7. The other enantiomer of 9 obtained from 7, with a retention time of 11 minutes, gave positive specific rotation. Once it was established that the enantiomer with the retention time of 9 minutes was the desired enantiomer of 7, this enantiomer was coupled with methylamine using HATU to provide the methyl amide, which under Boc deprotection conditions with trifluoroacetic acid (TFA) provided the pure enantiomer of compound 10.

Scheme 2

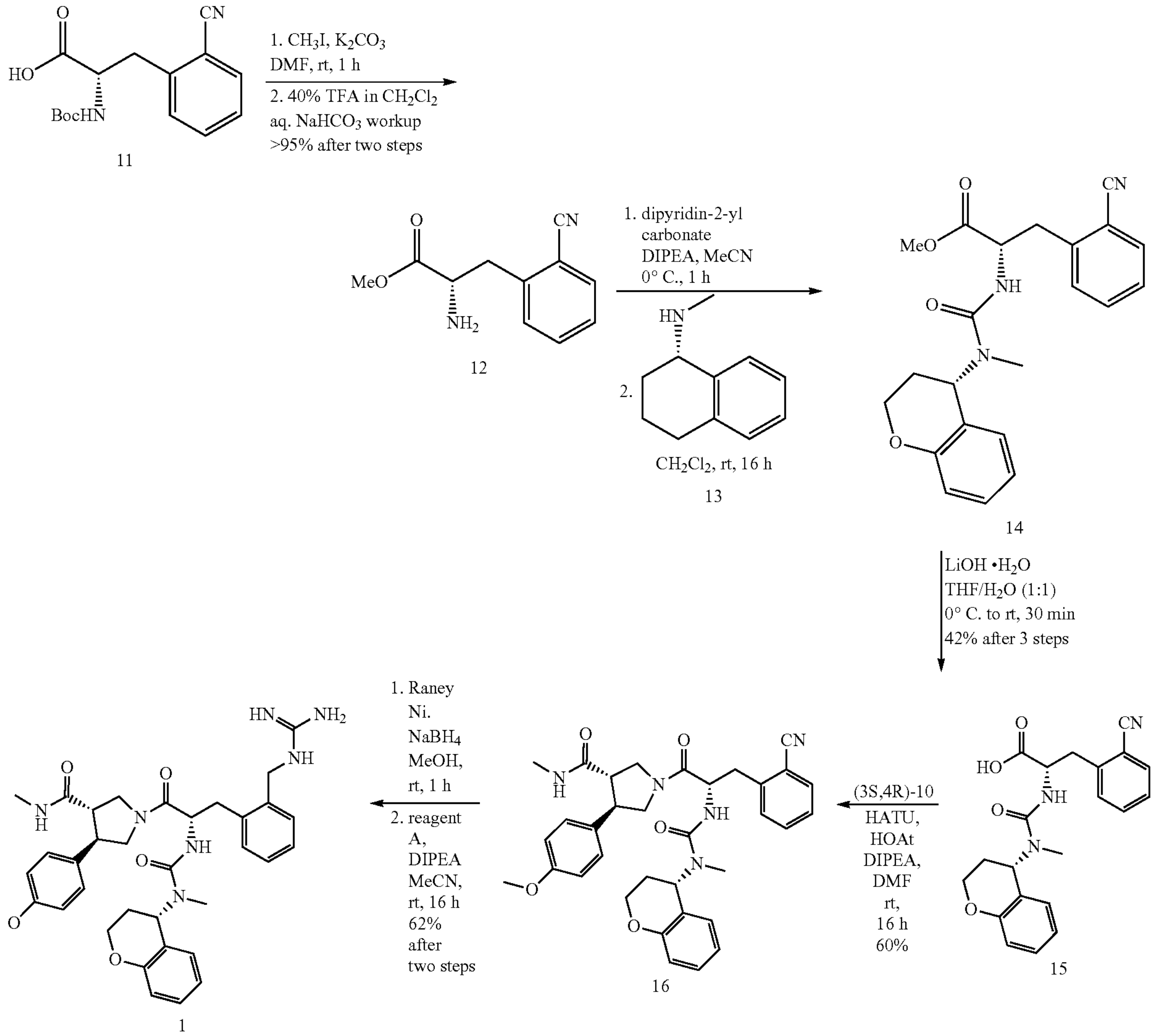

The synthesis of other part of the molecule started with compound 11, which was treated with iodomethane and potassium carbonate ($K_2CO_3$) to afford the methyl ester, which in turn under Boc deprotection conditions provided free amine 12. When 12 was treated with dipyridin-2-yl carbonate at 0° C., the amine was converted to isocyanate which when treated with freshly prepared secondary amine 13 afforded the urea 14. The primary amine 12 was prone to react with the isocyanate obtained from itself and produced the dimeric urea of 12 in 50% yield. Various purification methods were unable to separate the desired product 14 from this byproduct. Both 14 and the byproduct were taken for ester hydrolysis with lithium hydroxide (LiOH) at 0° C. Purification by normal phase chromatography afforded the acid 15 in 42% yield in 3-steps. It was confirmed that compound 15 was a pure stereoisomer by optical rotation and NMR. The acid 15 was then coupled with amine 10 using HATU to afford 16, which on nitrile reduction followed by guanidine formation with reagent A, provided the final product Compound 1. Compound 1 was purified by reverse-phase C-18 preparative HPLC and characterized before biological evaluation.

A detailed procedure for preparing Compound 1 is provided below.

Preparation of Common Intermediate 12

To a solution of 11 (290 mg, 1 mmol, 1 equiv.) in DMF (10 mL) was added anhydrous $K_2CO_3$ (415 mg, 3 mmol, 3 equiv.), and iodomethane (421 mg, 3 mmol, 3 equiv.) and the mixture was stirred at room temperature for 1 hour. The reaction mixture was filtered and concentrated under reduced pressure. Purification by flash chromatography ($SiO_2$, EtOAc/hexanes gradient) afforded the coupled product as a white foam. This product was dissolved in 40% TFA in $CH_2Cl_2$ (10 mL) and the mixture was stirred at room temperature for 30 minutes at which point the Boc deprotection was completed as monitored by LCMS. The reaction mixture was concentrated under reduced pressure, dissolved in $CH_2Cl_2$ and washed with saturated $NaHCO_3$ (10 mL). The organic layer was dried ($Na_2SO_4$) and concentrated under reduced pressure to afford the product 12 as a white solid (200 mg, >95%). H NMR (600 MHz, $CDCl_3$) δ 1.70 (br s, 2H), 3.05 (dd, J=13.9, 8.5 Hz, 1H), 3.30 (dd, J=13.7, 5.4 Hz, 1H), 3.72 (s, 3H), 3.82-3.80 (m, 1H), 7.34 (app t, J=7.6 Hz, 1H), 7.37 (app d, J=7.8 Hz, 1H), 7.53 (app t, J=7.6 Hz, 1H), 7.63 (app d, J=7.7 Hz, 1H); HRMS (ESI+) $[(M+H)^+]$ 205.0972.

Urea Formation and Ester Hydrolysis

Step 1: To a solution of common intermediate 12 (200 mg, 0.98 mmol, 1 equiv.) in MeCN (3 mL) was added DIPEA (348 μL, 1.98 mmol, 2 equiv.) and the mixture was cooled to 0° C. and stirred at that temperature for 10 minutes. Dipyridin-2-yl carbonate (440 mg, 2.0 mmol, 2 equiv.) was added and the mixture was stirred at 0° C. for 1 hour.

Step 2: To a solution of (S)-chroman-4-amine (free-amine, 200 mg, 1.34 mmol, 1 equiv.) in hexafluoroisopropanol (HFIP; 1.4 mL, 13.4 mmol, 10 equiv.) was added methyl triflate (230 μL, 2.01 mmol, 1.5 equiv.) and the mixture was stirred at room temperature for exactly 1 hour. The reaction mixture was quenched by adding 2N HCl (2 mL) and the volatiles were removed under reduced pressure. The mixture was neutralized by adding saturated $NaHCO_3$ and extracted with $CH_2Cl_2$ (3×5 mL). The combined organic layer was dried ($Na_2SO_4$) and concentrated under reduced pressure to afford the amine 13 as a pale yellow solid. The solid residue was dissolved in $CH_2Cl_2$ (3 mL) and added to the reaction mixture from step 1 and the mixture was stirred at room temperature for 16 hours. The reaction mixture was concentrated under reduced pressure and purification by flash chromatography ($SiO_2$, EtOAc/hexanes gradient) afforded a mixture of the desired methyl ester 14 and a dimeric urea byproduct (total 208 mg).

Step 3: To the solution of this mixture in step 2 above in THF (5 mL) was added $H_2O$ (5 mL) and the biphasic mixture was stirred vigorously at 0° C. for 10 minutes. $LiOH·H_2O$ (68 mg, 1.62 mmol, ~3 equiv.) was added and the mixture was stirred at room temperature for 30 minutes. The layers were separated and to the aqueous layer was added 1N HCl dropwise to adjust the pH to ~3. The aqueous layer was extracted with EtOAC and the combined organic layer was dried ($Na_2SO_4$) and concentrated under reduced pressure. Purification by flash chromatography ($SiO_2$, $MeOH/CH_2Cl_2$ gradient) afforded the product 15 as a white foam (155 mg, 42% after 3 steps). $^1H$ NMR (600 MHz, $CD_3OD$) S 1.97-1.93 (m, 1H), 2.12-2.06 (m, 1H), 2.55 (s, 3H), 3.26 (dd, J=13.8, 10.0 Hz, 1H), 3.57 (dd, J=13.9, 4.2 Hz, 1H), 4.11 (td, J=11.4, 1.8 Hz, 1H), 4.29 (dt, J=11.3, 3.7 Hz, 1H), 4.81 (dd, J=9.4, 3.8 Hz, 1H), 5.49 (dd, J=9.7, 6.5 Hz, 1H), 6.71 (br d, J=7.0 Hz, 11H), 6.74 (d, J=8.2 Hz, 1H), 6.82 (t, J=7.4 Hz, 1H), 7.09 (app t, J=7.9 Hz, 1H), 7.45 (t, J=7.6 Hz, 1H), 7.53 (d, J=7.8 Hz, 1H), 7.64 (t, J=7.6 Hz, 1H), 7.73 (d, J=7.4 Hz, 1H); HRMS (ESI+) $[(M+H)^+]$ 380.1605.

Preparation of Amine 10

The (±)-7 enantiomer separation was carried out using Agilent 1260 Infinity prep HPLC system equipped with CHIRALPAK IC (21×250 mm, 10 μm) preparative column (Agilent; Santa Clara, CA). Solvent system including heptane (A) and ethanol (B) were used under gradient conditions (5% B at 1.0 min to 40% B at 10.0 min to 95% B at 11.0 min) at a flow rate of 20 ml/min with a run time of 15 minutes. UV detection was performed at a wavelength of 220 nm with a peak width >0.025 min (0.5 s response time). The enantiomers were eluted at retention times of 9.4 min and 10.9 min respectively and collected using a prep scale fraction collector. The collected fractions were evaporated to obtain enantiomers of 7 as white solids. To a solution of 3S,4R-7 (100 mg, 0.311 mmol, 1 equiv., retention time 9.4 min) in DMF (6.2 mL) was added HOAt/DIPEA mixture (6.2 mL, 100 mM each in MeCN, 2 equiv.), HATU (236 mg, 0.622 mmol, 2 equiv.), and methylamine hydrochloride (42 mg, 0.622 mmol, 2 equiv.) and the mixture was stirred at room temperature for 1 hour. The reaction mixture was concentrated under reduced pressure, dissolved in EtOAc (10 mL), and washed with saturated $NaHCO_3$ (10 mL) and brine. The organic layer was dried ($Na_2SO_4$) and concentrated under reduced pressure. Purification by flash chromatography ($SiO_2$, $MeOH/CH_2Cl_2$ gradient) afforded the coupled product as a white foam. This product was dissolved in 40% TFA in $CH_2Cl_2$ (5 mL) and the mixture was stirred at room temperature for 30 minutes at which point the Boc deprotection was completed as monitored by LCMS. The reaction mixture was concentrated under reduced pressure and purified by C-18 reverse phase chromatography (10% MeCN/0.1% FA in $H_2O$ to 100% MeCN) to afford the product 10 as a white solid (67 mg, 92%). $^1H$ NMR (600 MHz, $CD_3OD$) δ 2.64 (s, 3H), 3.14 (app q, J=9.3 Hz, 1H), 3.35 (app t, J=11.4 Hz, 1H), 3.51-3.47 (m, 1H), 3.64-3.59 (m, 1H), 3.72-3.69 (m, 2H), 3.77 (s, 3H), 6.91 (d, J=8.7 Hz, 2H), 7.23 (d, J=8.7 Hz, 2H); HRMS (ESI+) $[(M+H)^+]$ 235.1441.

Amide Coupling

To a solution of 15 (29 mg, 0.077 mmol, 1 equiv.) in DMF (2 mL) was added HOAt/DIPEA mixture (1.54 mL, 100 mM each in MeCN, 2 equiv.), HATU (58 mg, 0.153 mmol, 2 equiv.), and a solution of 10 (29 mg, 0.123 mmol, 1.6 equiv.) in DMF (2 mL) and the mixture was stirred at room temperature for 16 hours. The reaction mixture was concentrated under reduced pressure, dissolved in EtOAc (10 mL), and washed with saturated $NaHCO_3$ (10 mL) and brine. The organic layer was dried ($Na_2SO_4$) and concentrated under reduced pressure. Purification by flash chromatography ($SiO_2$, $MeOH/CH_2Cl_2$ gradient) afforded the coupled product 16 as a colorless oil (27 mg, 60%). $^1H$ NMR (600 MHz, $CD_3OD$, observed as a mixture of rotamers) δ 1.93-1.86 (m, 1H), 2.11-2.03 (m, 1H), 2.57 (s, 3H), 2.63-2.61 (four singlets, 3H), 3.01 (app q, J=8.6 Hz, 0.61H), 3.09 (app q, J=7.9 Hz, 0.38H), 3.24 (dd, J=13.8, 9.2 Hz, 1H), 3.57-3.35 (m, 3H), 3.71 (t, J=10.6 Hz, 0.64H), 3.77-3.76 (two singlets, 3H), 3.87 (t, J=10.2 Hz, 0.4H), 3.97-3.92 (m, 1.2H), 4.04-4.00 (m, 0.8H), 4.13-4.07 (m, 1H), 4.29-4.26 (m, 1H), 4.99-4.95 (m, 0.62H), 5.10-5.07 (m, 0.38H), 5.47-5.44 (m, 1H), 6.54 (br dd, J=19.2, 7.2 Hz, 0.5H), 6.66 (br dd, J=20.0, 6.9 Hz, 0.5H), 6.75 (d, J=8.2 Hz, 1H), 6.89-6.81 (m, 3H), 7.10 (app t, J=7.7 Hz, 1H), 7.19-7.17 (m, 2H), 7.50-7.47 (m, 1H), 7.55 (d, J=7.5 Hz, 1H), 7.66 (app t, J=7.6 Hz, 1H), 7.75 (d, J=7.7 Hz, 1H), 7.96-7.90 (m, 0.7H); HRMS (ESI+) $[(M+H)^+]$ 596.2867.

Nitrile Reduction and Guanidine Formation

To a solution of 16 (18 mg, 0.030 mmol, 1 equiv.) in MeOH (4 mL) was added Raney Ni (25 μL, 50% wet in $H_2O$) followed by a freshly prepared solution of $NaBH_4$ (114 mg, 3.0 mmol, 100 equiv.) in MeOH (1 mL) and the mixture was stirred at room temperature for 1 hour. The reaction mixture was filtered through a short pad of Celite and concentrated under reduced pressure. The residue was fractionated between $H_2O$ and $CH_2Cl_2$. The organic layer was dried, evaporated and dissolved in MeCN (2 mL) and DIPEA (16 μL, 0.09 mmol, 3 equiv.) and 1H-pyrazole-1-carboximidamide hydrochloride (13 mg, 0.09 mmol, 3 equiv.) were added and the mixture was stirred at room temperature for 16 hours. The reaction mixture was concentrated under reduced pressure. Purification by C-18 reverse phase chromatography (10% MeCN/0.1% FA in $H_2O$ to 100% MeCN) afforded the product 1 as a white solid (12 mg, 62%) as a formate salt. $^1H$ NMR (600 MHz, $CD_3OD$, observed as a mixture of rotamers) δ 1.95-1.88 (m, 1H), 2.13-2.07 (m, 1H), 2.61-2.57 (three singlets, 6H), 2.82 (app q, J=9.7 Hz, 0.36H), 2.96 (app q, J=9.4 Hz, 0.72H), 3.14-3.08 (m, 1.7H), 3.54-3.21 (m, 5.3H), 2.77-2.75 (two singlets, 3H), 3.87 (dd, J=12.2, 8.3 Hz, 0.8H), 3.98 (dd, J=12.0, 8.0 Hz, 0.3H), 4.14-4.09 (m, 1H), 4.33-4.29 (m, 1H), 4.55 (ABq, Δδ=60.9 Hz, J=15.1 Hz, 1.5H), 4.62 (ABq, Δδ=96.6 Hz, J=15.4 Hz, 1.5H), 4.81 (submerged in $H_2O$ peak, 0.63H), 5.03 (app t, J=8.0 Hz, 0.37H), 5.52-5.49 (m, 1H), 6.57-6.55 (m, 0.27H), 6.69-6.67 (m, 0.76H), 6.76-6.74 (m, 1H), 6.88-6.82 (m, 3H), 7.12-7.07 (m, 3H), 7.47-7.34 (m, 4H), 8.44 (br s, 1.3H, formate ion); HRMS (ESI+) $[(M+H)^+]$ 642.3398.

Example 2: Synthesis of Compound 2-6

Compounds 2-6 were synthesized using the procedures described above for the synthesis of Compound 1. The common intermediate 12 was used for the formation of desired urea, followed by methyl ester hydrolysis. Compounds 5 and 6 were prepared by nitrile reduction followed by guanidine formation while keeping the carboxylic acid intact whereas Compounds 2, 3, and 4 were prepared by amide coupling of the carboxylic acid followed by nitrile reduction, and guanidine formation.

Example 3: Thrombin Inhibition of Compounds

The inhibitory potency of Compound 1 on thrombin was tested in vitro. Argatroban, a known small molecule direct thrombin inhibitor, was used as a control. See Table 1 and FIG. 1.

TABLE 1

| Compound | Thrombin $K_i$app (nM) |
|---|---|
| Argatroban | 9.0 ± 0.5 |
| Compound 1 | 1.0 ± 0.03 |

Compound 1 inhibited thrombin very strongly with an inhibition constant of 1 nM. Compound 1 was about 10-fold more potent than argatroban, which had an inhibition constant of 9.0 nM (FIG. 1).

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus, a combination of steps, elements, components, or constituents can be explicitly mentioned herein; however, all other combinations of steps, elements, components, and constituents are included, even though not explicitly stated.

What is claimed is:

1. A compound of the following formula:

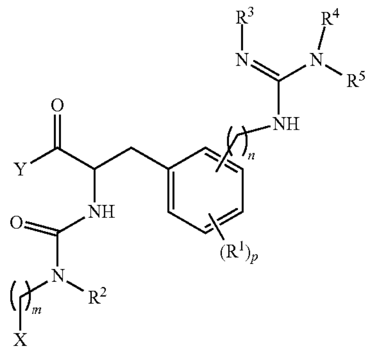

or a pharmaceutically acceptable salt or prodrug thereof, wherein:

m and n are each independently 0, 1, or 2;

p is 1, 2, 3, or 4;

X is substituted or unsubstituted aryl, substituted or unsubstituted heteroaryl, substituted or unsubstituted cycloalkyl, or substituted or unsubstituted heterocycloalkyl;

Y is hydroxy, alkoxy, aryloxy, substituted or unsubstituted amino, substituted or unsubstituted cycloalkyl, or substituted or unsubstituted heterocycloalkyl;

each $R^1$ is independently selected from the group consisting of hydrogen, halogen, cyano, trifluoromethyl, alkoxy, aryloxy, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^2$, $R^3$, $R^4$, and $R^5$ are each independently selected from the group consisting of hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

2. The compound of claim 1, wherein $R^3$, $R^4$, and $R^5$ are each hydrogen.

3. The compound of claim 1, wherein $R^2$ is methyl.

4. The compound of claim 1, wherein X is substituted or unsubstituted phenyl.

5. The compound of claim 1, wherein X is substituted or unsubstituted chromanyl.

6. The compound of claim 1, wherein n is 1.

7. The compound of claim 1, wherein the compound has the following formula:

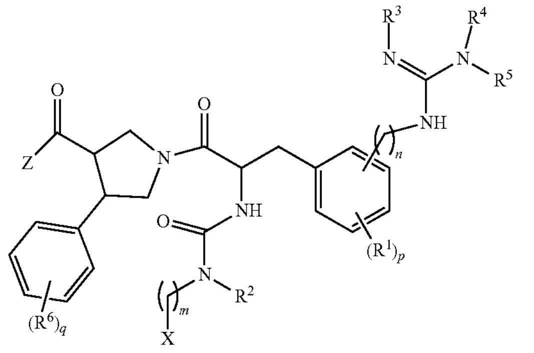

or a pharmaceutically acceptable salt or prodrug thereof, wherein:

q is 1, 2, 3, 4, or 5;

each $R^6$ is independently selected from the group consisting of hydrogen, halogen, cyano, trifluoromethyl, alkoxy, aryloxy, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and Z is —$NR^7R^8$ or —$OR^7$, wherein $R^7$ and $R^8$ are each independently selected from the group consisting of hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

8. The compound of claim 7, wherein $R^2$ is methyl.

9. The compound of claim 7, wherein $R^6$ is alkoxy.

10. The compound of claim 7, wherein $R^6$ is p-methoxy.

11. The compound of claim 7, wherein the compound has the following formula:

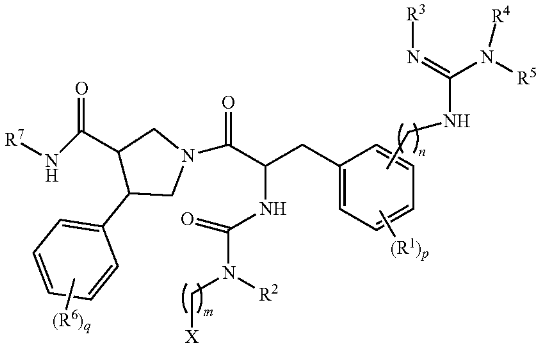

or a pharmaceutically acceptable salt or prodrug thereof.

12. The compound of claim 7, wherein the compound has the following formula:

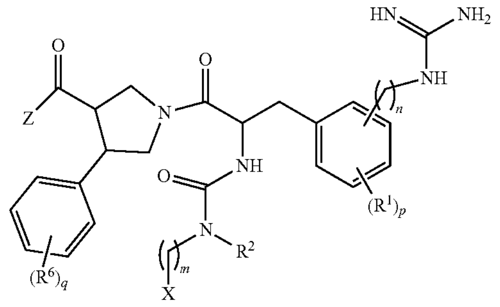

or a pharmaceutically acceptable salt or prodrug thereof.

13. The compound of claim 7, wherein the compound has the following formula:

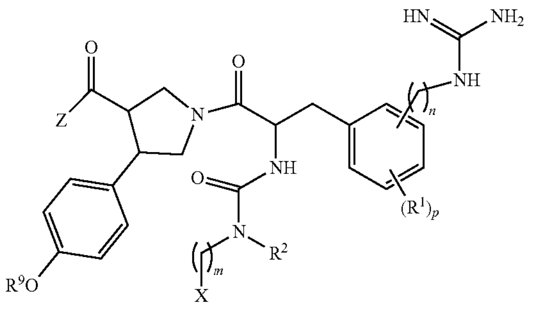

or a pharmaceutically acceptable salt or prodrug thereof, wherein:

$R^9$ is substituted or unsubstituted alkyl or substituted or unsubstituted aryl.

14. The compound of claim 7, wherein the compound has the following formula:

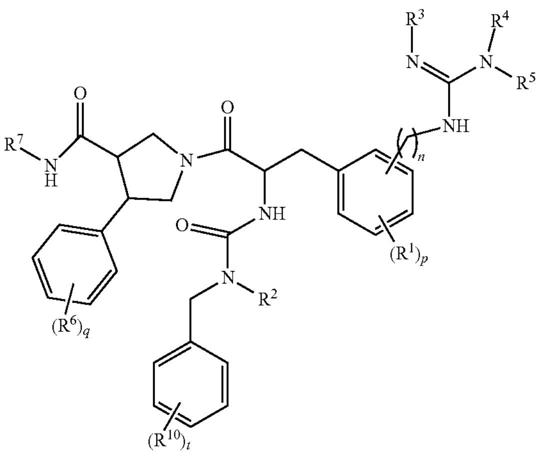

or a pharmaceutically acceptable salt or prodrug thereof, wherein:

t is 0, 1, 2, 3, 4, or 5; and each $R^{10}$ is independently selected from the group consisting of hydrogen, halogen, cyano, trifluoromethyl, alkoxy, aryloxy, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

15. The compound of claim 7, wherein the compound has the following formula:

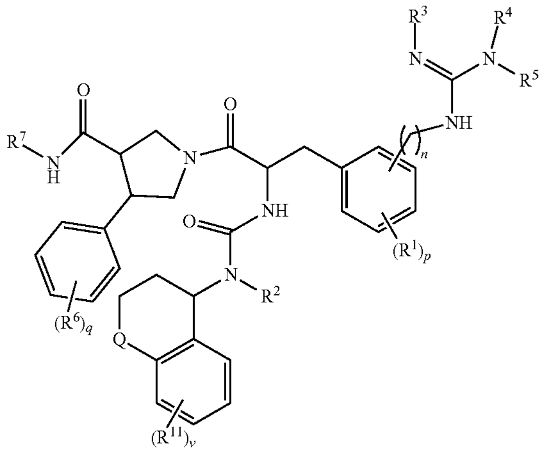

or a pharmaceutically acceptable salt or prodrug thereof, wherein:

Q is $CH_2$, O, or NH;

v is 0, 1, 2, 3, or 4; and each $R^{11}$ is independently selected from the group consisting of hydrogen, halogen, cyano, trifluoromethyl, alkoxy, aryloxy, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

16. The compound of claim 1, wherein the compound has the following formula:

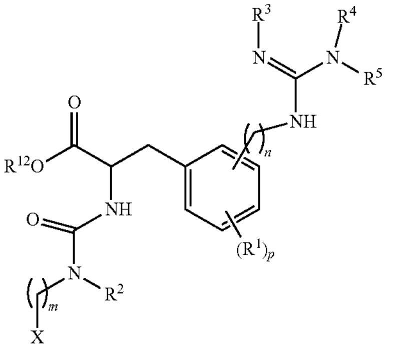

or a pharmaceutically acceptable salt or prodrug thereof, wherein:

$R^{12}$ is hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl.

17. The compound of claim 1, wherein the compound has the following formula:

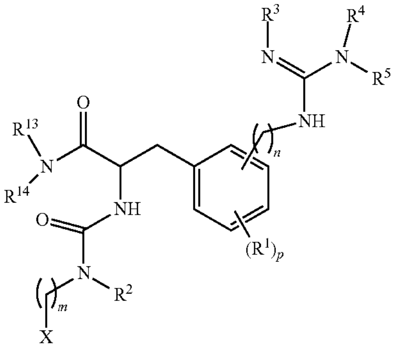

or a pharmaceutically acceptable salt or prodrug thereof, wherein:

$R^{13}$ and $R^{14}$ are each independently selected from the group consisting of hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

18. The compound of claim 1, wherein the compound is selected from the group consisting of:

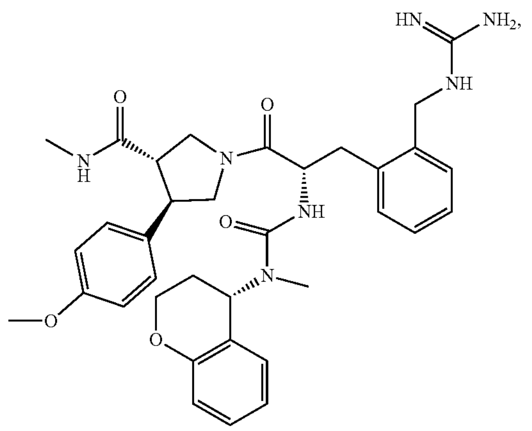
,

-continued
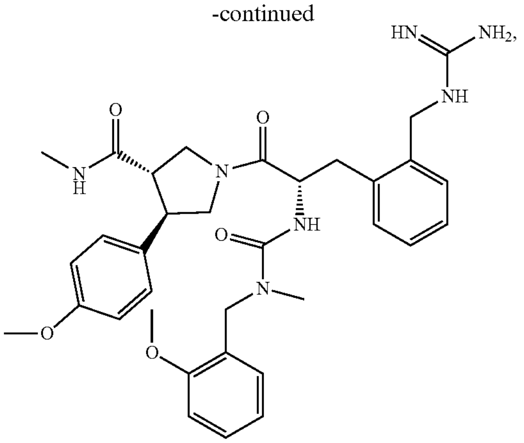
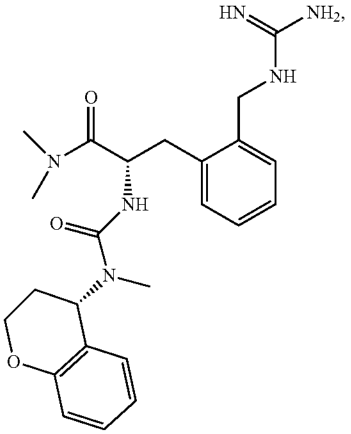
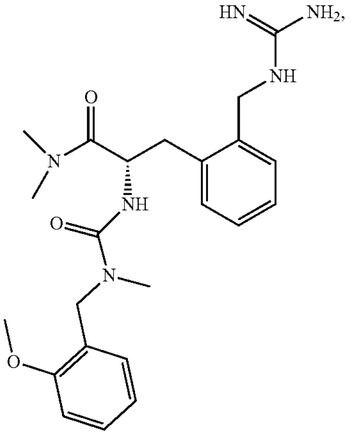
-continued
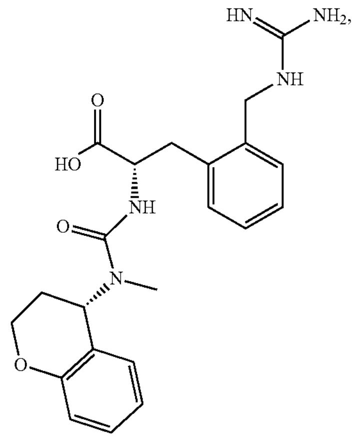
and
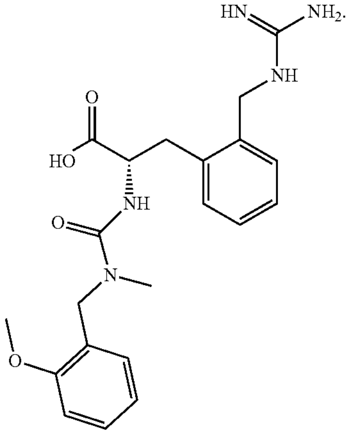
19. A pharmaceutical composition, comprising a compound of claim 1 and a pharmaceutically acceptable carrier.
20. A kit comprising a compound of claim 1 or a pharmaceutical composition of claim 19.
* * * * *